United States Patent
Casado et al.

(10) Patent No.: US 6,635,780 B1
(45) Date of Patent: Oct. 21, 2003

(54) CHEMICAL PROCESSES

(75) Inventors: Michel Casado, St. Symphorien d'Ozon (FR); Patrick Ratton, Mions (FR); Dominique Stephan, Meyzieu (FR); Agnès Viauvy, Saint Andeol le Chateau (FR)

(73) Assignee: Bayer CropScience S.A., Lyons (FR)

( * ) Notice: Subject to any disclaimer, the term of this patent is extended or adjusted under 35 U.S.C. 154(b) by 0 days.

(21) Appl. No.: 09/807,274

(22) PCT Filed: Oct. 11, 1999

(86) PCT No.: PCT/EP99/08135
§ 371 (c)(1),
(2), (4) Date: Jun. 14, 2001

(87) PCT Pub. No.: WO00/21922
PCT Pub. Date: Apr. 20, 2000

(30) Foreign Application Priority Data

| Oct. 13, 1998 | (EP) | 98420185 |
| Oct. 13, 1998 | (EP) | 98420186 |
| Oct. 13, 1998 | (EP) | 98420187 |

(51) Int. Cl.$^7$ .......................................... C07C 253/14

(52) U.S. Cl. ............................................... 558/343

(58) Field of Search ........................................ 558/343

(56) References Cited

U.S. PATENT DOCUMENTS

| 2,716,646 A | * | 8/1955 | Willett et al. ............ 260/294.9 |
| 3,890,326 A | | 6/1975 | Tobin |
| 4,211,721 A | * | 7/1980 | Cotter .......................... 260/465 |
| 4,886,936 A | * | 12/1989 | Dinizo .......................... 558/343 |
| 5,386,051 A | * | 1/1995 | Beck et al. ................... 558/343 |
| 5,474,998 A | | 12/1995 | Harrison et al. |
| 5,478,963 A | | 12/1995 | Pfirmann et al. |
| 5,492,875 A | | 2/1996 | Schach et al. |
| 5,705,674 A | * | 1/1998 | Wessel et al. ............... 558/343 |

FOREIGN PATENT DOCUMENTS

| EP | 0 110 559 A1 | 6/1984 |
| EP | 0 608 713 A1 | 8/1994 |
| EP | 0 635 303 A1 | 1/1995 |
| EP | 0 758 643 A2 | 2/1997 |
| JP | 03090057 A1 | 4/1991 |

OTHER PUBLICATIONS

Thomson Derwent; English language abstract of JP 56079662 (1993).

Thomson Derwent; English language abstract of JP 01153669 (1993).

* cited by examiner

*Primary Examiner*—Joseph K. McKane
*Assistant Examiner*—Kamal Saeed
(74) *Attorney, Agent, or Firm*—Connolly Bove Lodge & Hutz LLP

(57) ABSTRACT

The invention relates to a process for the preparation of a compound of formula (I)

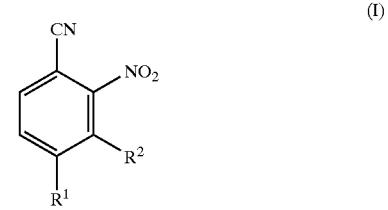

wherein:

R$^1$ represents C$_{1-4}$ haloalkyl, fluorine, chlorine or bromine; and R$^2$ represents hydrogen or C$_{1-4}$ alkoxy; which process comprises the reaction of the corresponding ortho-nitrohalobenzene of formula (II):

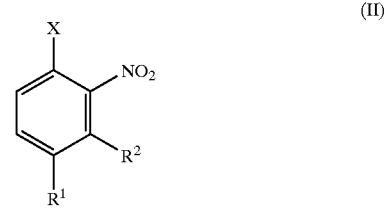

wherein R$^1$ and R$^2$ are as hereinbefore defined and X represents a fluorine or bromine atom, with, when X represents a fluorine atom:
(a) an alkali metal cyanide, in a non aqueous solvent, optionally in the presence of a catalyst; or when X represents a bromine atom:
(b) cuprous cyanide, in a non aqueous solvent, optionally in the presence of a catalyst selected from an alkali metal bromide or an alkaline earth metal bromide; or
(c) an alkali metal cyanide, in a non aqueous solvent, in the presence of a catalytic amount of cuprous cyanide and a phase transfer catalyst.

14 Claims, No Drawings

CHEMICAL PROCESSES

This application is a 371 of PCT/BP99/08135 filed of Oct. 11, 1999.

This invention relates to novel processes for preparing intermediates (particuiarly 4-cyano-3-nitrobenzotrifluoride) useful in the preparation of pesticides.

Pesticidal 4-benzolisoxazoles, particularly 5-cyclopropylisoxazole herbicides and intermediate compounds in their synthesis, are described in the literature, for example in European Patent Publication Nos. 0418175, 0487353, 0527036, 0560482, 0609798 and 0682659.

Various methods for preparing these compounds are known. The present invention seeks to provide improved methods for the preparation of pesticides and the intermediate compounds useful in preparing them.

It is therefore an object of the present invention to provide novel and more economical processes for the preparation of ortho-nitrobenzonitrile compounds.

It is a further object of the present invention to provide processes for the preparation of ortho-nitrobenzonitrile compounds which proceed in high yield and/or with high selectivity.

It is a further object of the present invention to provide a process for the preparation of ortho-nitrobenzonitrile compounds which requires a low amount of copper compound as catalyst.

It is a further object of the present invention to provide a process for the preparation of ortho-nitrobenzonitrile compounds which proceeds using cuprous cyanide without the need for a catalyst.

It is a further object of the present invention to provide a process for the preparation of ortho-nitrobenzonitrile compounds which proceeds at a lower temperature than known methods and therefore easier to perform.

The present invention allows these objects to be met in whole or in part.

SUMMARY OF THE INVENTION

The present invention accordingly provides a process for the preparation of an ortho-nitrobenzonitrile compound of formula (I):

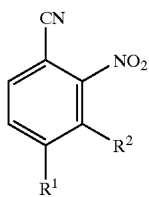

(I)

wherein:

$R^1$ represents $C_{1-4}$ haloalkyl (preferably trifluoromethyl), fluorine, chlorine or bromine; and R2 represents hydrogen or $C_{1-4}$ alkoxy; which process comprises the reaction of the corresponding ortho-nitrohalobenzene of formula (II):

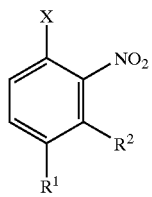

(II)

wherein $R_1$ and $R^2$ are as hereinbefore defined and X represents a fluorine, chlorine or bromine atom, with when X represents a flourine atom:
a) an alkali metal cyanide, in a non aqueous solvent optionally in the presence of a catalyst; or when X represents a chlorine atom:
(b) cuprous cyanide and a source of bromide selected from hydrogen bromide, bromine and a tetraalkylammonium bromide; optionally in the presence of an alkali metal bromide or an alkaline earth metal bromide; or
(c) an alkali metal cyanide or a tetraalkylammonium cyanide, in the presence of cuprous bromide and a phase transfer catalyst; or
(d) cuprous cyanide and lithium iodide; or when X represents a bromine atom:
(e) cuprous cyanide optionally in the presence of a catalyst selected from an alkali metal bromide or an alkaline earth metal bromide; or
(f) an alkali metal cyanide in the presence of a catalytic amount of cuprous cyanide and a phase transfer catalyst.

Certain compounds of formula (I) are known and a number of processes for their preparation and conversion into herbicidal 4-benzoylisoxazole derivatives have been described in the European Patent Applications cited above.

Compounds of formula (II) are known or may be prepared by known methods.

In formulae (I) and (II) and in the formulae depicted hereinafter, preferred values of the symbols are as follows:

Preferably $R^1$ represents trifluoromethyl, fluorine or bromine; and $R^2$ represents hydrogen or methoxy.

In a particularly preferred embodiment of the invention $R^1$ represents trifluoromethyl and $R^2$ represents hydrogen.

It is to be understood that in this invention the term "alkyl" which forms part of tetralkylammonium salts represents a straight-or branched-chain alkyl group containing from one to six carbon atoms.

DETAILED DESCRIPTION OF THE INVENTION

The above preparation a) of compounds of formula (I) from compounds of formula (II) wherein X represents a fluorine atom is performed with an alkali metal cyanide (for example sodium cyanide or potassium cyanide). Sodium cyanide is preferred. The amount of cyanide used is generally from 1–2 molar equivalents, preferably from 1–1.1 molar equivalents.

A number of non-aqueous solvents are suitable, for example nitrites such as acetonitrile or benzonitrile; ethers such as tetrahydrofuran or diglyme (diethylene glycol dimethyl ether); amides such as N,N-dimethylformamide or N-methylpyrrolidone; ketones such as methyl isobutyl ketone; esters such as methyl benzoate or n-butyl acetate; dimethylsulphoxide or sulpholane. Preferably the solvent is chosen from benzonitrile, acetonitrile, tetrahydrofuran or N,N-dimethylformamide.

The reaction is generally conducted in a solvent with less than about 1% by volume water content preferably less than about 0.5%, even more preferably less than about 0.1%, typically from about 0.005 to about 0.05%. It will however be understood that in certain cases slightly more or less water may be tolerated, depending on the nature of the solvents used and the temperature of the reaction, the compound of formula (I) to be prepared and other reaction conditions.

Preferably a catalyst is used, which may be selected from ammonium salts (such as tetraalkylammonium or trialkylbenzylammonium chlorides, bromides or hydrogen sulphate salts, in which the alkyl groups are straight- or branched-chain containing from one to six carbon atoms, such as tetramethylammonium bromide); or preferably guanidinium salts (such as hexabutylguanidinium chloride or hexamethylguanidinium chloride). The amount of catalyst when employed is generally from 0.01 to 0.3 molar equivalent, preferably from 0.05–0.25 molar equivalent.

Generally the reaction temperature is from 20° C. to the boiling point of the solvent, preferably from 30° C. to 180° C., and more preferably from 60° C. to 100° C.

The above preparation (b) of compounds of formula (I) from compounds of formula (II) wherein X represents a chlorine atom is performed with cuprous cyanide and a source of bromide selected from hydrogen bromide, bromine and a tetraalkylammonium bromide, optionally in the presence of an alkali metal bromide or an alkaline earth metal bromide, preferably lithium bromide. In this process the amount of cuprous cyanide used is generally from 0.5–2 molar equivalents and preferably from 0.8–1.2 molar equivalents.

The amount of bromide source used is generally from 0.05–1 molar equivalent.

When an alkali metal bromide or an alkaline earth metal bromide is also present in the reaction mixture it is used in catalytic amount, generally from 0.01–0.5 molar equivalents and preferably from 0.02–0.05 molar equivalents.

The solvent may be chosen from nitriles such as acetonitrile or benzonitrile; ketones such as methyl isobutyl ketone; ethers such as tetrahydrofuran or diglyme (diethylene glycol dimethyl ether); esters such as methyl benzoate or n-butyl acetate; dimethylsulphoxide or sulpholane. Preferred solvents are acetonitrile, benzonitrile or diglyme.

The concentration of the compound of formula (II) used in the reaction solvent is generally in the range from 0.1 ml/mmol to 2 ml/mmol, and preferably from 0.2 ml/mmol to 1 ml/mmol.

The reaction temperature is generally from 100° C. to 200° C., preferably from 130° C. to 180° C.

The above preparation (c) of compounds of formula (I) from compounds of formula (II) wherein X represents a chlorine atom is performed with an alkali metal cyanide (for example sodium cyanide or potassium cyanide) or a tetraalkylammonium cyanide, in the presence of cuprous bromide and a phase transfer catalyst.

Preferably the alkali metal cyanide is potassium cyanide. The amount of alkali metal cyanide or tetraalkylammonium cyanide used is generally 1–1.5 molar equivalents (preferably 1–1.1 molar equivalents. The amount of cuprous bromide used is generally from 0.01–2 molar equivalents (preferably 1 molar equivalent). The reaction is conducted using solid liquid phase transfer catalysis. The phase transfer catalyst may be selected from tetraalkylammonium salts or trialkylbenzylammonium salts (such as tetramethylammonium bromide or benzyltrimethylammonium bromide); phosphonium salts (such as tributylhexadecylphosphonium bromide); guanidinium salts (such as hexabutylguaridinium bromide or hexamethylguanidinium bromide); and crown ethers (such as 18-crown-6). The amount of phase transfer catalyst used is generally from 0.05–0.3 molar equivalents. Suitable solvents for the reaction include nitriles such as acetonitrile or benzonitrile; ethers such as tetrahydrofuran or diglyme (diethylene glycol dimethyl ether); ketones such as methyl isobutyl ketone; or esters such as methyl benzoate. The preferred solvent is acetonitrile.

The concentration of the compound of formula (II) used in the reaction solvent is generally in the range from 0.1 ml/mmol to 2 ml/mmol, and preferably from 0.2 ml/mmol to 1 ml/mmol.

The reaction temperature is generally from 100° C. to 200° C., preferably from 130° C. to 180° C.

The above preparation (d) of compounds of formula (I) from compounds of formula (II) wherein X represents a chlorine atom is performed using cuprous cyanide and lithium iodide. Generally from 0.5–2 molar equivalents (preferably from 0.8–1.2 molar equivalents) of cuprous cyanide is employed in the reaction. The amount of lithium iodide employed is generally from 0.05 to 2 molar equivalents, preferably from 0.2 to 0.5 molar equivalents.

Suitable solvents for the reaction include nitriles such as benzonitrile or acetonitrile; ethers such as diglyme (diethylene glycol dimethyl ether); ketones such as methyl isobutyl ketone; or esters such as methyl benzoate.

The reaction temperature is generally from 100° C. to 200° C., preferably from 130° C. to 180° C.

The above preparation (e) of compounds of formula (I) from compounds of formula (II) wherein X represents a bromine atom is performed using cuprous cyanide optionally in the presence of a catalyst selected from an alkali metal bromide or an alkaline earth metal bromide, preferably lithium bromide. Generally from 0.5–2 molar equivalents (preferably 1–1.1 molar equivalents) of cuprous cyanide is employed in the reaction. The amount of catalyst employed (when present) is generally from 0.05 to 2 molar equivalents.

Suitable solvents for the reaction include nitriles such as acetonitrile or benzonitrile; ethers such as tetrahydrofuran or diglyme (diethylene glycol dimethyl ether); ketones such as methyl isobutyl ketone; esters such as methyl benzoate or n-butyl acetate; amides such as N,N-dimethylformamide or N-methylpyrrolidone; dimethylsulphoxide or sulpholane. Preferred solvents are acetonitrile, benzonitrile or tetrahydrofuran.

The reaction temperature is generally from 100° C. to 200° C., preferably from 110° C. to 160° C. (more preferably 120° C. to 140° C.).

The compound of formula (II) used in the reaction may contain a proportion (generally up to 20%) of the corresponding compound in which the bromine atom is replaced by a chlorine atom. It has been found that this is not detrimental to the reaction. It may therefore be more convenient or straightforward to purify and isolate the nitrile compound of formula (I) rather than using a pure compound of formula (II). This separation may be achieved by standard procedures known in the art, for example by distillation.

The above preparation (f) of compounds of formula (I) from compounds of formula (II) wherein X represents a bromine atom is performed using an alkali metal cyanide in the presence of a catalytic amount of cuprous cyanide and a phase transfer catalyst. Potassium cyanide is the preferred alkali metal cyanide. The amount of cuprous cyanide used is generally from 0.05 to 0.2 molar equivalents. The amount of alkali metal cyanide used is generally from 0.5–2 molar equivalents, preferably from 0.6–1.3 molar equivalents (more preferably 0.7–1 molar equivalents). The phase transfer catalyst may be selected from alkali metal bromides or alkaline earth metal bromides, preferably lithium bromide; tetraalkylammonium bromides or trialkylbenzylammonium bromides, in which the alkyl groups are straight- or branched-chain containing from one to six carbon atoms (such as tetramethylammonium bromide or benzyltrimethylammonium bromide); phosphonium salts (such as tributylhexadecylphosphonium bromide); guanidinium salts such as (hexabutylguanidinium bromide or hexamethylguanidinuim bromede); and crown ethers (such as 18-crown-6). The amount of phase transfer catalyst used is generally from 0.05–0.5 molar equivalents (preferably from 0.05–0.3 molar equivalents.

Suitable solvents for the reaction include nitriles such as acetonitrile or benzonitrile; alcohols such as n-butanol; amides such as N,N-dimethylformamide or N-methylpyrrolidone; ketones such as methyl isobutyl ketone; esters such as methyl benzoate; ethers such as tetrahydrofuran or diglyme (diethylene glycol dimethyl ether) dimethylsulphoxide or sulpholane.

The concentration of the compound of formula (II) used in the reaction solvent is generally in the range from 0.1 ml/mmol to 2 ml/mmol, preferably from 0.2 ml/mmol to 1 ml/mmol, more preferably from 0.2 ml/mmol to 0.4 ml/mmol.

The reaction temperature is generally from 100° C. to 200° C., preferably from 110° C. to 160° C.

According to a further feature of the present invention there is provided a process (g) for the preparation of a compound of formula (II) wherein $R^1$ and $R^2$ are as hereinbefore defined and X represents a bromine atom, which comprises the reaction of the corresponding compound of formula (II) in which X represents a chlorine atom, with a bromide source.

Examples of suitable bromide sources include alkali metal bromides (such as potassium bromide or lithium bromide); alkaline earth metal bromides (such as magnesium bromide); cuprous bromide; cupric bromide; zinc bromide; hydrogen bromide; or bromine; or a mixture of lithium bromide and cuprous bromide. The preferred bromide source is a mixture of lithium bromide and cuprous bromide; or magnesium bromide or cupric bromide. The amount of bromide source used is generally one to five molar equivalents. When a mixture of lithium bromide and cuprous bromide is used, 0.1–1 molar equivalents of cuprous bromide is generally employed, together with one to two molar equivalents of lithium bromide.

A solvent is generally required to obtain good results. Suitable solvents for the reaction include nitrites such as acetonitrile or benzonitrile; ethers such as tetrahydrofuran or diglyme (diethylene glycol dimethyl ether); ketones such as methyl isobutyl ketone; esters such as methyl benzoate or n-butyl acetate; N-methylpyrrolidone; alkanoic acids such as acetic acid; dimethylsulphoxide and sulpholane.

The reaction temperature is generally from 100° C. to 200° C., preferably from 130° C. to 180° C. Good results are obtained when the process is carried out in a concentrated medium.

According to a further feature of the present invention processes (e) or (f) can be combined with process (g) to prepare a compound of formula (I) starting from a compound of formula (II) wherein X represents a chlorine atom.

The compounds of formula (I) obtained by the processes of the present invention may be used in the preparation of herbicidally active 4-benzoylisoxazole derivatives for example according to the following reaction scheme:

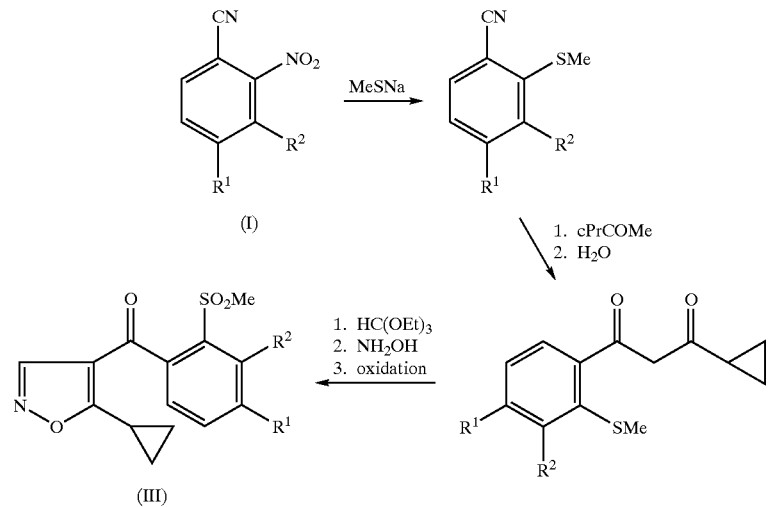

The 4-benzoylisoxazoles of formula (III) are described in for example European Patent Publication Nos. 0418175, 0527036 and 0560482.

The following non-limiting examples illustrate the invention. Where concentrations of ingredients in solvent are given these are understood to refer to the concentration of the compound of formula (II) in the solvent (i.e. ml of solvent/mmol of compound of formula (II)).

EXAMPLE 1

Preparation of 4-cyano-3-nitrobenzotrifluoride from 4-Fluoro-3-nitrobenzotrifluoride Using an Alkali Metal Cyanide (Process (a))

A mixture of 4-fluoro-3-nitrobenzotrifluoride (1 mmol) and sodium cyanide or potassium cyanide (1 mmol), and acetonitrile or benzonitrile (1 ml/mmol) were mixed at 20° C. and heated for 6 hours at 80° C. to give the title product. The results are shown in Table 1, from which it can me seen that the use of sodium cyanide gives good selectivity.

TABLE 1

| Cyanide | Solvent | Conversion (%) | Yield (%) | Selectivity (%) |
|---------|---------|----------------|-----------|-----------------|
| NaCN    | CH3CN   | 79             | 45        | 57              |
| KCN     | CH3CN   | 76             | 38        | 49              |
| NaCN    | PhCN    | 45             | 36        | 80              |
| KCN     | PhCN    | 35             | 26        | 74              |

EXAMPLE 2

Preparation of 4-Cyano-3-nitrobenzotrifluoride from 4-Fluoro-3-nitrobenzotrifluoride Using Sodium Cyanide: Effect of Solvent, Temperature and Catalyst (Process (a))

A mixture of 4-fluoro-3-nitrobenzotrifluoride (1 mmol) and sodium cyanide (1 mmol) and N,N-dimethylformamide, acetonitrile, tetrahydrofuran or benzonitrile (1 ml/mmol) were mixed at 20° C. and heated for 6 hours to give the title product. The results are shown in Table 2, from which it may be observed that benzonitrile (PhCN) gave the highest selectivity.

TABLE 2

| Solvent | Temp (° C.) | Conversion (%) | Yield (%) | Selectivity (%) |
|---------|-------------|----------------|-----------|-----------------|
| DMF     | 80          | 95             | 35        | 37              |
| DMF     | 40          | 83             | 38        | 46              |
| DMF     | 25–30       | 80             | 31        | 39              |
| CH3CN   | 80          | 79             | 45        | 57              |
| THF     | 80          | 69             | 39        | 56              |
| PhCN    | 80          | 45             | 36        | 80              |

The above experimental procedure was repeated at 80° C. but in the presence of a catalyst (0.2 equivalent) and acetonitrile, tetrahydrofuran or benzonitrile (1 ml/mmol). The catalysts used were hexabutylguanidinium chloride or tetrabutylammonium bromide. The results (shown in Table 3) indicate that the use of hexabutylguanidinium chloride as catalyst gave very good selectivity especially in tetrahydrofuran or benzonitrile.

TABLE 3

| Catalyst | Solvent | Time | Conversion (%) | Yield (%) | Selectivity (%) |
|----------|---------|------|----------------|-----------|-----------------|
| (a)      | CH3CN   | 13 h | 47             | 33        | 70              |
| (a)      | THF     | 6 h  | 45             | 40        | 90              |
| (a)      | PhCN    | 6 h  | 42             | 40        | 95              |
| (b)      | CH3CN   | 13 h | 88             | 47        | 54              |

(a) = hexabutylguanidinium chloride
(b) = tetrabutylammonium bromide.

EXAMPLE 3

Preparation of 4-Cyano-3-nitrobenzotrifluoride from 4-Chloro-3-nitrobenzotrifluoride Using Cuprous Cyanide and a Source of Bromide (Process (b))

A mixture of 4-chloro-3-nitrobenzotrifluoride (1 or 1.3 equivalents), cuprous cyanide (1 equivalent) and bromine (optionally in the presence of a catalytic amount of lithium bromide) or hydrogen bromide (47% aqueous) were mixed in benzonitrile (2 equivalents) at 20° C. and heated at 170° C. to give the title product. The results are shown in Table 4. The selectivity in these reactions was at least 90%.

TABLE 4

| ClTNB (Eq) | Source of bromide | | Time | Conversion/CuCN |
|------------|-------------------|---|------|-----------------|
| 1 eq       | Br2               | 0.1 eq  | 7 h  | 67%  |
| 1.3 eq     | Br2               | 0.25 eq | 11 h | 100% |
|            | LiBr              | 0.05 eq |      |      |
| 1 eq       | HBr aq(47%)       | 0.5 eq  | 8 h  | 62%  |

ClTNB=4-chloro-3-nitrobenzotrifluoride.

The above procedure was repeated using 4-chloro-3-nitrobenzotrifluoride (1 equivalent), cuprous cyanide (1 equivalent) and benzyltrimethylammonium bromide (1 equivalent) in acetonitrile (1 ml/mmol) with heating at 160° C. for 6 hours to give the title compound. The conversion of 4-chloro-3-nitrobenzotrifluoride was 94%, the yield of product 62% and the selectivity 66%.

The above experiment was repeated but with the following modifications; cuprous cyanide (1 equivalent) and tert-butylamine hydrobromide (1 equivalent) in benzonitrile (2 equivalents) were mixed at 20° C. then heated to 150° C. 4-Chloro-3-nitrobenzotrifluoride (1.2 equivalents) was then added during 1 hour and the mixture maintained at that temperature for 7 hours. It may be seen (Table 5) that when these conditions are used, the reaction proceeds with good selectivity.

TABLE 5

| tBuNH3.Br | Conversion/CuCN | Selectivity |
|-----------|-----------------|-------------|
| 1 eq      | 87%             | 90%         |

EXAMPLE 4

Preparation of 4-Cyano-3-nitrobenzotrifluoride from 4-Chloro-3-nitrobenzotrifluoride Using an Alkali Metal Cyanide, Cuprous Bromide and a Phase Transfer Catalyst (Process (c))

A mixture of 4-chloro-3-nitrobenzotrifluoride (1 equivalent), potassium cyanide (1 equivalent), cuprous bromide (1 equivalent) and a quaternary ammonium salt (0.2 equivalents) was mixed at 20° C. then heated with acetonitrile (1 ml/mmol) at 160° C. for 8 hours to give the title product. Table shows the results from which it may be seen that good selectivity is obtained using these conditions.

TABLE 6

| R4N.Br | Conversion (%) | Yield (%) | Selectivity (%) |
|--------|----------------|-----------|-----------------|
| (a)    | 80             | 64        | 80              |
| (b)    | 79             | 66        | 84              |

(a) tetraethylammonium bromide
(b) benzyltrimethylammonium bromide

EXAMPLE 5

Preparation of 4-Cyano-3-nitrobenzotrifluoride from 4-Chloro-3-nitrobenzotrifluoride Using Cuprous Cyanide and Lithium Iodide (Process (d))

A mixture of 4-chloro-3-nitrobenzotrifluoride (1 equivalent), cuprous cyanide (1 equivalent) and lithium iodide (0.2 or 0.5 equivalents) was heated with benzonitrile or diglyme (diethylene glycol dimethyl ether) (1 ml/mmol) for 6 hours at 160° C. to give the title product. Lithium iodide was chosen for its solubility in organic solvents. Table 7 shows the results from which it may be observed that a particularly good selectivity is obtained using 0.5 equivalents of lithium iodide.

TABLE 7

| Solvent | LiI | Conversion (%) | Yield (%) | Selectivity (%) |
| --- | --- | --- | --- | --- |
| PhCN | 0.5 eq | 62 | 62 | ≧95 |
| Diglyme | 0.5 eq | 70 | 70 | ≧95 |
| PhCN | 0.2 eq | 59 | 56 | 95 |
| Diglyme | 0.2 eq | 37 | 32 | 86 |

EXAMPLE 6

Preparation of 4-Cyano-3-nitrobenzotrifluoride from 4-Bromo-3-nitrobenzotrifluoride Using Cuprous Cyanide Optionally in the Presence of Lithium Bromide (Process (e))

A mixture of 4-bromo-3-nitrobenzotrifluoride (1 equivalent) and cuprous cyanide (1 equivalent), optionally in the presence of lithium bromide (1 equivalent) and benzonitrile or tetrahydrofuran (1 ml/mmol) was heated at 130° C. for 6 hours to give the title product. The results (Table 8) show that excellent yields and selectivity are obtained using these conditions, either with or without the catalyst.

TABLE 8

| Solvent | LiBr | Conversion (%) | Yield (%) | Selectivity (%) |
| --- | --- | --- | --- | --- |
| Benzonitrile | 1 eq | 95 | 92 | 97 |
| Benzonitrile | — | 96 | 96 | 100 |
| THF | 1 eq | 97 | 97 | 100 |

The above experiment was repeated using benzonitrile or acetonitrile (1 ml/mmol) at 110° C. The lithium bromide improves the solubility of cuprous cyanide in the organic solvent but excellent results have been obtained (Table 9) with or without the lithium bromide.

TABLE 9

| Solvent | ml/mmol | LiBr | Conversion (%) | Yield (%) | Selectivity (%) |
| --- | --- | --- | --- | --- | --- |
| PhCN | 1 | — | 84 | 85 | ≧95 |
| PhCN | 1 | 1 eq | 89 | 88 | ≧95 |
| CH3CN | 1 | — | 92 | 93 | ≧95 |
| CH3CN | 1 | 1 eq | 91 | 91 | ≧95 |
| PhCN | 0.2 | — | 96 | 95 | ≧95 |
| PhCN | 0.2 | 1 eq | 98 | 98 | ≧95 |
| CH3CN | 0.2 | — | 96 | 94 | ≧95 |
| CH3CN | 0.2 | 1 eq | 98 | 98 | ≧95 |

EXAMPLE 7

Large Scale Preparation of 4-Cyano-3-nitrobenzotrifluoride from a Mixture of 4-Bromo-3-nitrobenzotrifluoride and 4-Chloro-3-nitrobenzotrifluoride Using Cuprous Cyanide (Process (e))

A mixture of 4-bromo-3-nitrobenzotrifluoride (0.2 equivalent, 1.7 mole, containing 12% of 4-chloro-3-nitrobenzotrifluoride) and cuprous cyanide (1.1 equivalent) was heated to 130° C., then the remaining 4-bromo-3-nitrobenzotrifluoride (0.8 equivalent) added during 4 hours at 130° C. After a further 2 hours at 130° C., the cooled mixture was extracted (toluene), washed (aqueous sodium bromide then sodium bisulphite) and evaporated to give the title product. The conversion and yield of title product (based on 4-bromo-3-nitrobenzotrifluoride content) were both 100%. The 4-chloro-3-nitrobenzotrifluoride remained unchanged.

EXAMPLE 8

Preparation of 4-Cyano-3-nitrobenzotrifluoride from 4-Bromo-3-nitrobenzotrifluoride Using Alkali Metal Cyanide and a Catalytic Amount of Cuprous Cyanide in the Presence of a Phase Transfer Catalyst (Process (f))

A mixture of 4-bromo-3-nitrobenzotrifluoride (1 equivalent), potassium cyanide (0.9 equivalent), cuprous cyanide (0.1 equivalent), and phase transfer catalyst (tetraethylammonium bromide or tetrabutylammonium bromide) was heated with benzonitrile, acetonitrile, n-butanol or dimethylsulphoxide at 110° C. for 6 hours. The results (Table 10) show that an excellent selectivity may be obtained using benzonitrile, acetonitrile or n-butanol at 0.2 ml/mmol or 0.4 m/mmol concentration. When a small amount of water (6 microlitres/mmol) was present in addition to the acetonitrile (at 0.4 ml/mmol) the yield of title product was increased to 44% with selectivity remaining at a high level.

TABLE 10

| Solvent | ml/mmol | Catalyst | eq | Conversion (%) | Yield (%) | Selectivity (%) |
| --- | --- | --- | --- | --- | --- | --- |
| PhCN | 0.2 | Et4NBr | 0.2 | 11 | 11 | ≧95 |
| PhCN | 0.2 | Bu4NBr | 0.2 | 11 | 11 | ≧95 |
| CH3CN | 0.2 | Et4NBr | 0.2 | 12 | 12 | ≧95 |
| CH3CN | 0.2 | Bu4NBr | 0.2 | 13 | 12 | ≧95 |
| CH3CN | 0.4 | Et4NBr | 0.1 | 17 | 18 | ≧95 |
| n-BuOH | 0.4 | Et4NBr | 0.1 | 15 | 15 | ≧95 |
| DMSO | 0.4 | Et4NBr | 0.1 | 92 | 32 | 35 |
| CH3CN | 0.4 (a) | Et4NBr | 0.1 | 49% | 44 | 89 |

(a) 6 microlitres of water/mmol were added to the acetonitrile in this experiment

EXAMPLE 9

Preparation of 4-Cyano-3-nitrobenzotrifluoride from 4-Bromo-3-nitrobenzotrifluoride Using Alkali Metal Cyanide and a Catalytic Amount of Cuprous Cyanide in the Presence of Lithium Bromide as a Phase Transfer Catalyst (Process (f))

A mixture of 4-bromo-3-nitrobenzotrifluoride (1 equivalent, 0.02 mole), potassium cyanide (1.2 equivalent, 0.024 mole), cuprous cyanide (0.1 equivalent, 0.002 mole), and lithium bromide (0.25 equivalent, 0.005 mole) was heated in 6 ml of acetonitrile at 110° C. for 18 hours after which time the starting 4-bromo-3-nitrobenzotrifluoride had been consumed. The cooled mixture was extracted (methyl tert-butyl ether), washed (water), dried magnesium sulphate) and evaporated to give the title product.

The conversion was 99%, and the yield of the product 89.7% with a puritan of 93.8%.

EXAMPLE 10

Preparation of 4-Bromo-3-nitrobenzotrifluoride from 4-Chloro-3-nitrobenzotrifluoride Using Various Bromide Sources (Process (g))

A mixture of 4-chloro-3-nitrobenzotrifluoride (1 equivalent) and a bromide source (cuprous bromide, cupric bromide, lithium bromide or magnesium bromide) (1 equivalent), or a mixture of cuprous bromide (1 equivalent) and lithium bromide (1 equivalent) was heated for 6 hours at 160° C. with benzonitrile, diglyme (diethylene glycol dimethyl ether), acetic acid or N-methylpyrrolidone (1 ml/mmol) to give the title product. Table 11 shows that good selectivity may be obtained using various conditions and that the mixture of cuprous bromide and lithium bromide gives particularly good results. By comparison poor results were obtained in the absence of solvent.

TABLE 11

| Solvent | Bromide | Conversion (%) | Yield (%) | Selectivity (%) |
|---|---|---|---|---|
| PhCN | CuBr | 17 | 11 | 63 |
| diglyme | CuBr | 8 | 7 | 86 |
| PhCN | CuBr2 | 18 | 15 | 84 |
| diglyme | CuBr2 | 15 | 12 | 80 |
| AcOH | CuBr2 | 17 | 16 | 95 |
| diglyme | LiBr | 23 | 21 | 89 |
| NMP | LiBr | 17 | 9 | 51 |
| NMP | MgBr2 | 30 | 21 | 71 |
| NMP (a) | MgBr2 | 35 | 32 | 91 |
| PhCN | CuBr + LiBr | 51 | 49 | 95 |
| diglyme | CuBr + LiBr | 24 | 20 | 83 |
| AcOH | CuBr + LiBr | 36 | 31 | 86 |
| NMP | CuBr + LiBr | 32 | 17 | 52 |
| (b) | CuBr + LiBr | 2 | 1 | — |

(a) 0.1 ml/mmol of NMP (N-methylpyrrolidone) were used in this experiment.
(b) no solvent used.

EXAMPLE 11

Preparation of 4-Bromo-3-nitrobenzotrifluoride from 4-Chloro-3-nitrobenzotrifluoride Using a Mixture of Cuprous Bromide and Lithium Bromide (Process (g))

The above procedure of Example 10 was repeated using a mixture of cuprous bromide (1 equivalent) and lithium bromide (1 equivalent) with various concentrations of benzonitrile (0.02, 0.04, 0.1, 0.5, 1 or 2 ml/mmol). Table 12 shows that good selectivity was obtained using all of these conditions and that when 0.04 ml/mmol of benzonitrile was present the conversion, yield and selectivity were particularly good.

TABLE 12

| PhCN ml/mmol | Conversion (%) | Yield (%) | Selectivity (%) |
|---|---|---|---|
| 2 | 43 | 40 | 93 |
| 1 | 51 | 49 | 95 |
| 0.5 | 61 | 58 | 95 |
| 0.1 | 59 | 56 | 95 |
| 0.04 | 70 | 68 | 97 |
| 0.02 | 20 | 18 | 87 |

The above reaction was repeated but using diglyme (diethylene glycol dimethyl ether) instead of benzonitrile at various concentrations (0.01, 0.02, 0.04, 0.08, 0.1, 0.5, 1 or 2 ml/mmol). Table 13 shows that the conversion, yield and selectivity were optimal at the 0.02–0.04 ml/mmol concentration.

TABLE 13

| Diglyme ml/mmol | Conversion (%) | Yield (%) | Selectivity (%) |
|---|---|---|---|
| 2 | 24 | 18 | 75 |
| 1 | 24 | 20 | 83 |
| 0.5 | 25 | 20 | 81 |
| 0.1 | 40 | 39 | 97 |
| 0.08 | 31 | 29 | 95 |
| 0.04 | 52 | 50 | 96 |
| 0.02 | 50 | 48 | 96 |
| 0.01 | 34 | 33 | 97 |

The above reaction was repeated but using acetic acid, acetonitrile or tetrahydrofuran instead of benzonitrile at various concentrations (0.02, 0.04, 0.1 and 1 ml/mmol). Table 14 shows the results, from which it may be seen that the optimal concentration depends upon the solvent, and that the best results were obtained at high concentration.

TABLE 14

| Solvent | ml/mmol | Conversion (%) | Yield (%) | Selectivity (%) |
|---|---|---|---|---|
| AcOH | 1 | 36 | 31 | 86 |
| AcOH | 0.1 | 39 | 36 | 91 |
| AcOH | 0.02 | 3 | 2 | — |
| CH3CN | 0.1 | 46 | 44 | 95 |
| CH3CN | 0.04 | 36 | 33 | 92 |
| CH3CN | 0.02 | 16 | 14 | 89 |
| THF | 0.1 | 47 | 40 | 84 |
| THF | 0.04 | 55 | 42 | 77 |
| THF | 0.02 | 43 | 38 | 89 |

EXAMPLE 12

Preparation of 4-Bromo-3-nitrobenzotrifluoride from 4-Chloro-3-nitrobenzotrifluoride Using Various Ratios of a Mixture of Cuprous Bromide and Lithium Bromide (Process (g))

A mixture of 4-chloro-3-nitrobenzotrifluoride (1 equivalent), cuprous bromide (1 equivalent) and lithium bromide (2 equivalents) in benzonitrile (4 equivalents) was heated at 180° C. for 5 hours. The cooled mixture was extracted with toluene, washed with an aqueous solution of sodium bromide and with sodium bisulphite solution, and evaporated to give the title product. The conversion (based on 4-chloro-3-nitrobenzotrifluoride) was 84%, the yield 78%, and the selectivity 93%.

The above reaction was repeated using cuprous bromide (0.1 equivalent) and lithium bromide (2 equivalents) giving a conversion of 83% and a selectivity of 90%.

What is claimed is:

1. A process for the preparation of a compound of formula (I):

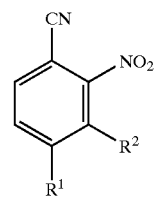

(I)

wherein:

R¹ represents $C_{1-4}$ haloalkyl, fluorine, chlorine or bromine; and R² represents hydrogen or $C_{1-4}$ alkoxy; which process comprises the reaction of the corresponding ortho-nitrohalobenzene of formula (II):

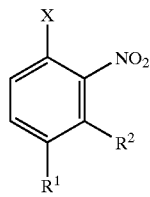

(II)

wherein R¹ and R² are as hereinbefore defined and X represents a fluorine or bromine atom, with, when X represents a fluorine atom:
(a) an alkali metal cyanide, in a non aqueous solvent, optionally in the presence of a catalyst; or
when X represents a bromine atom:
(b) cuprous cyanide, in a non aqueous solvent, optionally in the presence of a catalyst selected from an alkali metal bromide or an alkaline earth metal bromide.

2. A process according to claim 1 option (a) in which the catalyst is selected from ammonium salts, and guanidinium salts.

3. A process according to claim 1 option (a) in which the alkali metal cyanide is sodium cyanide.

4. A process according to claim 1 option (a), in which 1–2 molar equivalents of cyanide is used.

5. A process according to claim 1 option (a) in which the solvent is benzonitrile, acetonitrile, tetrahydrofuran or N,N-dimethylformamide.

6. A process according to claim 1 option (a) in which the solvent contains less than 1% by volume of water.

7. A process according to claim 1 option (b) in which the catalyst is lithium bromide.

8. A process according to claim 1 option (b) in which 0.5–2 molar equivalents of cuprous cyanide is used.

9. A process according to claim 1 option (b), in which the amount of catalyst is from 0.05–2 molar equivalents.

10. A process according to claim 1 option (b) in which the concentration of the compound of formula (II) used in the reaction solvent is from 0.1 ml/mmol to 2 ml/mmol.

11. A process according to claim 1 in which R¹ represents trifluoromethyl, fluorine or bromine; and R² represents hydrogen or methoxy.

12. A process according to claim 1 in which R¹ represents trifluoromethyl; and R² represents hydrogen.

13. A process according to claim 1 option (a) in which the concentration of the compound of formula (II) used in the reaction solvent is from 0.1 ml/mmol to 2 ml/mmol.

14. A process according to claim 1 option (b) wherein the non aqueous solvent is selected from the group consisting of acetonitrile, benzonitrile, tetrahydrofuran, diglyme, methyl isobutyl ketone, methyl benzoate, n-butyl acetate, N,N-dimethylformamide, N-methylpyrrolidone, dimethylsulphoxide and sulpholane.

* * * * *